United States Patent
Kumar et al.

(10) Patent No.: US 9,576,860 B2
(45) Date of Patent: Feb. 21, 2017

(54) METHOD AND APPARATUS PROVIDING INLINE PHOTOLUMINESCENCE ANALYSIS OF A PHOTOVOLTAIC DEVICE

(71) Applicant: FIRST SOLAR, INC, Perrysburg, OH (US)

(72) Inventors: Navneet Kumar, Maumee, OH (US); Amir Weiss, Sunnyvale, CA (US)

(73) Assignee: FIRST SOLAR, INC., Perrysburg, OH (US)

( * ) Notice: Subject to any disclaimer, the term of this patent is extended or adjusted under 35 U.S.C. 154(b) by 110 days.

(21) Appl. No.: 14/205,810

(22) Filed: Mar. 12, 2014

(65) Prior Publication Data

US 2014/0273313 A1 Sep. 18, 2014

Related U.S. Application Data

(60) Provisional application No. 61/789,223, filed on Mar. 15, 2013.

(51) Int. Cl.
*H01L 31/042* (2014.01)
*H01L 21/66* (2006.01)
*G01N 21/64* (2006.01)
*H01L 31/18* (2006.01)

(52) U.S. Cl.
CPC .......... *H01L 22/10* (2013.01); *G01N 21/6456* (2013.01); *G01N 21/6489* (2013.01); *H01L 31/18* (2013.01)

(58) Field of Classification Search
CPC ............................ H01L 31/042; H01L 25/042
See application file for complete search history.

(56) References Cited

U.S. PATENT DOCUMENTS

| | | |
|---|---|---|
| 2011/0025839 A1 | 2/2011 | Trupke et al. |
| 2011/0117681 A1 | 5/2011 | Bardos et al. |
| 2012/0025100 A1 | 2/2012 | Allenic et al. |

FOREIGN PATENT DOCUMENTS

WO WO 2012/016233 A1 2/2012

OTHER PUBLICATIONS

O. Vigil-Galán et al., "Physical Properties of Bi Doped CdTe Thin Films Grown by CSVT and Their Influence on the CdS/CdTe Solar Cells PV-Properties", Thin Solid Films, vol. 515, No. 15, Apr. 27, 2007, pp. 5819-5823.
Katherine Zaunbrecher et al., "Non-Uniformities in Thin-Film Cadmium Telluride Solar Cells using Electroluminescence and Photoluminescence", Photovoltaic Specialists Conference, Jun. 19, 2011, pp. 2841-2844.
S. Binetti et al., "Processing Step-Related Upgrading of Silicon-Based Solar Cells Detected by Photoluminescence Spectroscopy", Solar Energy Materials and Solar Cells, vol. 86, No. 1, Feb. 15, 2005, pp. 11-18.

*Primary Examiner* — Mohammad Choudhry
(74) *Attorney, Agent, or Firm* — Blank Rome LLP

(57) ABSTRACT

A method and apparatus are disclosed which use a photoluminescent light intensity signature to characterize a processed photovoltaic substrate.

30 Claims, 7 Drawing Sheets

METHOD AND APPARATUS PROVIDING INLINE PHOTOLUMINESCENCE ANALYSIS OF A PHOTOVOLTAIC DEVICE

CROSS-REFERENCE TO RELATED APPLICATION

This application claims priority to U.S. Provisional Application No. 61/789,223, filed Mar. 15, 2013, which is hereby fully incorporated by reference.

FIELD OF THE INVENTION

The invention relates to an in-line method and measurement tool which uses photoluminescence to determine characteristics of a photovoltaic device, such as photovoltaic cells and photovoltaic modules containing a plurality of photovoltaic cells.

BACKGROUND OF THE INVENTION

Photoluminescence (PL) is a process in which a substance absorbs photons and then re-radiates photons. Photoluminescent measurement is a contactless and non-destructive method of probing an electronic structure of materials.

Photoluminescence may be used to determine the quality of semiconductor material deposition on a substrate. For example, in thin-film photovoltaic device fabrication, semiconductor window and absorber layer materials are deposited over a substrate. Following deposition the substrate can then be irradiated by shining light into the substrate and measuring the photoluminescent spectrum which can indicate the quality of the semiconductor material depositions. After semiconductor deposition, photovoltaic devices are further fabricated in subsequent multiple steps. A measurement method and apparatus are needed which can detect deviations from desired processing conditions during such further fabrication of a photovoltaic device.

DETAILED DESCRIPTION OF THE INVENTION

The various embodiments described herein provide a photoluminescent method and apparatus for determining deviations from desired processing conditions which occur subsequent to semiconductor layer deposition on a substrate during the manufacture of photovoltaic device. Measurements of the photoluminescent spectra intensity are taken of the photovoltaic device in-line and at a stage after all processing of the photovoltaic internal layers is complete, for example, following completion of photovoltaic device fabrication.

These measurements can reveal, among other things, deviation in a desired processing condition such as deviation from a desired doping concentration for the absorber layer or deviation from a desired temperature used to heat treat a fabricated metallization pattern formed on the absorber layer.

Figure 1:
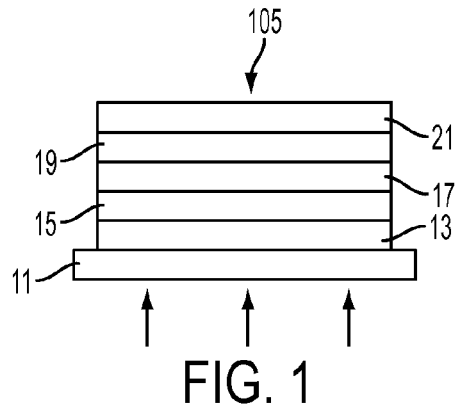
FIG. 1 illustrates one example of a coated substrate for use in forming a completed thin film photovoltaic device.

The manufacture of thin-film photovoltaic devices involves many, often complex, processing steps. These steps include, among others, the deposition and treatment of the various films which are deposited over a substrate. FIG. 1 illustrates one example of a partially fabricated thin-film photovoltaic device 105. The partially fabricated photovoltaic device 105 can be used to form one or more photovoltaic cells of a completed photovoltaic device. Device 105 includes a substrate 11 through which light, illustrated by the arrows, can pass which can be formed of a glass such as soda lime glass, low iron glass, solar float glass, or other suitable glass. A barrier layer 13 may be formed over the substrate 11 which is used to lessen the diffusion of sodium from the substrate into other layers of a completed photovoltaic device. The barrier layer 15 may include, for example, silicon dioxide ($SiO_2$), silicon aluminum oxide (SiAlO), in tin oxide (SiO) or other suitable material. A transparent conductive oxide (TCO) layer 15 can be deposited over the barrier layer 13 and is used as one conductor of a completed photovoltaic device. TCO layer 15 may be formed, for example, of cadmium stannate ($Cd_2SnO_4$), cadmium tin oxide ($CdO_3Sn$), fluorine (F) doped tin oxide (SnO), or other known transparent conductive oxide material. A buffer layer 17 may also be deposited over the TCO layer 15 to provide a smooth surface for deposition of semiconductor material. The buffer layer may include, for example, tin oxide ($SnO_2$), zinc tin oxide ($ZnSnO_3$), zinc oxide (ZnO) or zinc magnesium oxide (ZnMgO).

An n-type semiconductor material, forming a window layer 19, may then be deposited over the buffer layer 17. Although various known n-type semiconductor materials can be used, such as for example, ZnO, ZnS, ZnSe, ZnTe, CdO, CdS, CdSe, CdTe, MgO, MgS, MgSe, MgTe, HgO, HgS, HgSe, HgTe, MnO, MnS, MnTe, AlN, AlP, AlA, AlSb, GaN, GaP, GaAs, GaSb, InN, InP, InAs, InSb, TlN, TlP, TlAs, TlSb, or mixtures or alloys thereof, one which is particularly suitable is cadmium sulfide (CdS). A p-type semiconductor material is then provided over the window layer 19 and serves as an absorber layer 21. The absorber layer 21 converts photons into electrons and holes which are separated by the P/N junction formed at the interface between the n-type window layer 19 and p-type absorber layer 21. The absorber layer 21 can also be formed of known p-type semiconductor materials, for example, ZnO, ZnS, ZnSe, ZnTe, CdO, CdS, CdSe, CdTe, MgO, MgS, MgSe, MgTe, HgO, HgS, HgSe, HgTe, MnO, MnS, MnTe, MN, AlP, AlA, AlSb, GaN, GaP, GaAs, GaSb, InN, InP, InAs, InSb, TlN, TlP, TlAs, TlSb, CIG or CIGS or mixtures or alloys thereof, with cadmium telluride (CdTe) being one such material.

The absorber layer 21 is typically annealed by depositing a cadmium chloride solution ($CdCl_2$) in liquid form on the absorber layer 21 after which the absorber layer 21 is annealed by heat treatment at about 400 degrees C. to about 450 degrees C. for a predetermined period of time, for example, about 10 minutes to about one hour. The $CdCl_2$ anneal desirably increases the grain size of the absorber layer 21 which has been found to enhance photo-conversion efficiency.

Since the deposition of the semiconductor materials forming the window 19 and absorber 21 layers is important to the functionality and long term stability of a completed photovoltaic device, methods and apparatuses for monitoring the quality of those depositions have been developed. One such apparatus, which uses photoluminescence, is described in U.S. application Ser. No. 13/195,163, filed Aug. 1, 2011. The entirety of this application is fully incorporated herein by reference. The techniques described in the '163 application can provide useful information on the quality, uniformity and stability of the semiconductor window 19 and absorber 21 layer depositions shown in FIG. 1 by measuring the overall intensity of the photoluminescence.

Figure 2:
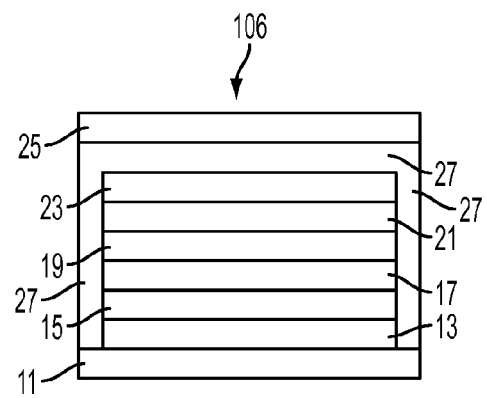
FIG. 2 illustrates one example of a completed thin-film photovoltaic device.

However, there are also subsequent fabrication steps which must further occur to produce a completed photovoltaic device. FIG. 2 illustrates an example of a completed photovoltaic device 106 fabricated from the partially fabricated device 105 shown in FIG. 1. The partially fabricated photovoltaic device 105 has been further processed to include, among other things, a copper doping of the absorber layer 21, the formation of a back contact (metallization) layer 23 over the absorber layer, and the provision of a back cover over the back contact layer 23. An interlayer material 27 may also be provided on the sides of the fabricated layers 13 through 21 and optionally also between the back contact layer 23 and back cover 25. The fabrication steps required to copper dope the absorber layer, as well as the process steps required to form the back contact 23, which include a heat treatment of the deposited back contact 23, can also affect quality and stability of the completed photovoltaic device 106. For example, improper copper doping concentration or non-uniform copper doping of the absorber layer 21 can affect electrical performance of the completed photovoltaic device 106, as well as long term stability. The copper doping is used to increase charge mobility in the absorber layer 21 and reduces that contact resistance between the absorber layer 21 and the metal contact layer 23. Moreover, during the back contact formation process heat is used to drive a deposited metal into the absorber layer 21 to provide a good contact therewith. The temperature of this heating process may also affect the quality of the contact and thus metal/absorber layer performance and quality and stability of the completed photovoltaic device 106.

Embodiments of the invention use a photoluminescence (PL) tool at the back end of a photovoltaic device manufacturing line and after processing of the internal layers of the photovoltaic device is completed to detect and measure the intensity of a photoluminescence spectra which can indicate deviations in process conditions subsequent to the deposition and $CdCl_2$ anneal treatment of absorber layer 21. Deviations which can be detected include, among others, deviations in a desired copper doping concentration and deviations in the heating temperature for back contact metallization.

Figure 3:
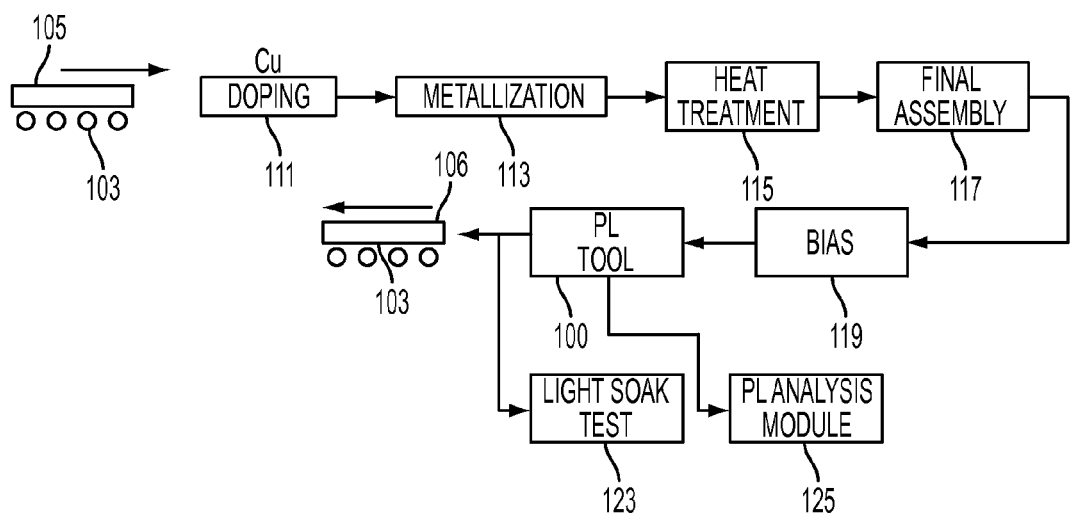
FIG. 3 illustrates a fabrication line which produces a photovoltaic device in accordance with an embodiment of the invention.

FIG. 3 schematically illustrates the processing of a partially fabricated device 105 (FIG. 1) towards a completed photovoltaic device 106 (FIG. 2). The partially completed PV device 105, following a $CdCl_2$ deposition and anneal of absorber layer 21, is conveyed by conveying mechanism 103, for example by driven rollers, to and through the various stages illustrated in FIG. 3. The partially completed photovoltaic device following the $CdCl_2$ anneal treatment, is provided to a doping station 111 at which copper doping is applied to the absorber layer 21. Following this, the partially completed photovoltaic device 105 proceeds to a metallization stage 113 where the back metal contacts 23 are applied. An optional ZnTe layer may also be deposited after the $CdCl_2$ treatment of the absorber layer, with or without copper doping, and before the metallization stage 113. Subsequent to the metallization stage 113, a heat treatment is applied at heat treatment stage 115 to drive metal applied in the metallization stage 113 into the absorber layer, after which a final photovoltaic device assembly is performed at stage 117. At the final assembly stage 117 the interlayer 27 and back cover 25 are applied and the substrate 11 and back cover 5 of the completed photovoltaic device 106 are laminated together. The final module assembly stage 117 also provides an edge seal to the completed photovoltaic device 106, and adds a cord plate or junction box over an opening in the back cover 25 to provide electrical connections to the one or more photovoltaic cells of the completed photovoltaic device 106.

Following final assembly at stage 117, the completed photovoltaic device 106 is subject to a biasing operation at bias stage 119 at which bias voltages are applied to the completed photovoltaic device 106 to condition the completed photovoltaic device 106 for use. Embodiments of the invention provide a photoluminescence tool 100 in-line, after processing of all internal material layers is completed, such as after final assembly of completed photovoltaic devices 106. Alternatively, the photoluminescence tool 100 can be provided in-line before bias stage 119. After passing the photoluminescence tool 100 and biasing stage 119, the completed photovoltaic devices 106 are passed to customer fulfillment.

In many instances sample testing of a few of the completed photovoltaic devices 106, using a so-called light soak test may occur at stage 123. In such a testing, some, but not all, of the completed photovoltaic devices 106 are removed from the production line and are tested over periods of days or weeks to determine how well other like completed photovoltaic devices 106 will perform in the field. While this testing does provide useful information on the quality of the completed photovoltaic devices 106, it is done on a sample basis and takes considerable time, and not all completed photovoltaic devices 106 are subject to the test. By contrast, the photoluminescent (PL) analysis tool 100 can provide qualitative information for each completed photovoltaic device 106 which can be used to determine deviations from certain post $CdCl_2$ anneal process conditions, to provide an indication of the quality and stability of completed photovoltaic devices 106 leaving the production line.

The provision of the photoluminescent (PL) tool 100 in-situ and in-line in particular enables an assessment of deviations from a proper copper doping concentration of the absorber layer 21 at stage 111 as well as temperature deviations at heat treatment stage 115. Thus, the photoluminescent tool 100 can provide, information on the quality and stability of each completed photovoltaic device 106 as a result of the doping 111, metallization 113, and heat treatment 115 stages. Such information can be gathered in real-time such that any abnormalities can be detected as a completed PV device 106 leaves the production line.

Figure 4:
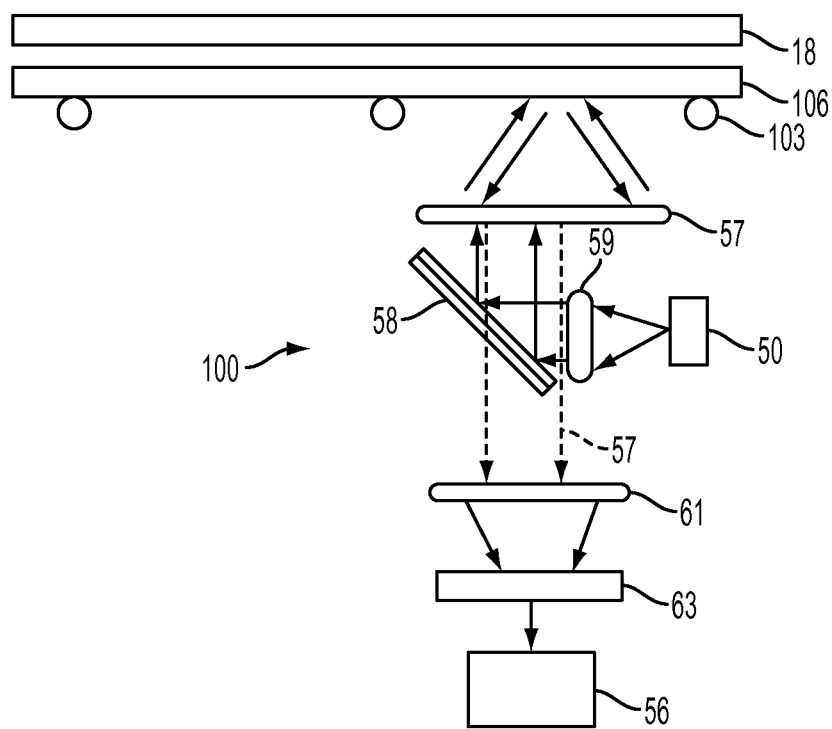
FIG. 4 illustrates a photoluminescence tool which can be used in an embodiment of the invention.

FIG. 4 shows an embodiment of a photoluminescent (PL) tool 100 which can be used. The PL tool 100 is provided beneath a conveyed completed photovoltaic device 106 and includes a monochromatic light source 50 which can be a light emitting diode, a diode laser or a solid state laser. Light source 50 can also comprise a white light source placed ahead of a monochromator. The wavelength of the light source 50 can be chosen depending on the band gap of one or more semiconductor materials contained within photovoltaic device 106. For example, light source 50 can be one of a red, blue or green color wavelength and can be chosen based on the band gap of one or more of the window layer 19, absorber layer 21, or interface between these layers. It is well known that a CdS window layer 19 and a CdTe absorber layer 21, during deposition and CdCl$_2$ absorber layer 21 annealing, can create a CdS$_x$Te$_{1-x}$ intermediate interface layer between window layer 19 and absorber layer 21.

The tool 100 further includes an optical system 59 employing various lenses and filters and which are used to supply a focus and/or collimated beam of light to the completed photovoltaic device 106. The optical system 59 can also reduce variations of the wave-length distribution and can consist, for example, of at least one plano-convex lens and a band-pass filter. The band-pass filter can be positioned between light source 50 and the optical system 59, or it can be integrated into the optical system 59 or provided at any other suitable position. The band-pass filter or filters can be optional and the decision to include them or not can be based on the wavelength of light from the light source 50 and/or a particular desired photoluminescence activation wavelength. The measurement tool 100 can further include an optical mirror 58, such as a dichroic mirror, which is used to redirect the light beam from source 50 and optical system 59 toward the completed photovoltaic device 106. The measurement tool 100 can further include a lens 57 chosen and positioned so that the desired focus position of the light beam irradiates one of the window layer 19, absorber layer 21 or interface between them, as desired. In some embodiments, slight over or under focus of the light beam can be acceptable so that more than one of the window 19 absorber 21 or intermediate layers are irradiated. As explained below, the intensity and wavelength of light can also be used to select which of the layers is irradiated. Lens 57 can also be optional depending on the beam collimation and distance to the semiconductor material layers within the completed photovoltaic device 106.

Light source 50 can emit light of any suitable wavelength. For example, light source 50 can emit red light having a wavelength between 600 nm and 690 nm, for example, at about 660 nm. Light source 50 can also emit blue light with a wavelength in the range of about 425 nm to about 490 nm, such as about 445 nm, as an example. Light source 50 can also emit green light having a wavelength in the range of about 500 nm to about 580 nm, for example, at about 532 nm.

The red light can pass through the CdS window layer 19 and CdS and CdS$_x$Te$_{1-x}$ intermediate interface layer such that photoluminescence spectra is primarily generated by the CdTe absorber layer 21. Blue light and green light can be absorbed by all three layers, but since the window and intermediate layers are first irradiated by incident light the resultant photoluminescence spectra is primarily from those two layers.

Semiconductor materials, such as at the window layer 19, absorber layer 21, and the interface between them, can be excited by the light beam impinging upon one or more of these layers provided by lens 57. The process of light emission following excitation of the semiconductor material with light (photons) of energy greater than its band gap is a result of recombination of photo generated electron and hole carriers produced by the photons from light source 50. Light emission depends on internal and external quantum efficiencies of each semiconductor layer. If the excited device consists of a bi-layer of material, for example, of a p-type semiconductor absorber layer 21 deposited on an n-type semiconductor window layer 19 which also has an interface layer, then the recombination can occur at various locations depending on excitation light intensity, wavelength, and resulting penetration into the layered semiconductor structure. Thus, by selecting the wavelength of the light source 50 and the focus characteristics of lens 57 one or more of the window layer 19, e.g., CdS, absorber layer 21, e.g., CdTe, and the interface, CdS$_x$Te$_{1-x}$, between them can be irradiated and photoluminescent intensity values obtained.

In addition, the wavelength of light incident on the completed photovoltaic device 106 can be changed by suitable light source 50 selection, band-pass filter selection and/or changes in the optic system 59 and 57 to select different excitation wavelengths, and focal points which can yield different degrees of penetration into the completed photovoltaic device 106. For example, the excitation light wavelength, intensity and/or focal point can be changed to examine one or more of the window layer 19, absorber layer 21 or interface layer between them, as the photovoltaic device 106 passes across the focal point of lens 57 during its movement by conveying mechanism 103.

The measurement tool 100 further includes a sensor 56 for sensing photons produced by the photoluminescence from the completed photovoltaic device 106 and an optical system 61 and band-pass filter 63 which are provided in front of the sensor 56. The optical system 61 can be provided by any suitable combination of lenses and band-pass filter 63 can be provided by one or more band-pass filter which combination can allow a specific region of the wavelength distribution of the photoluminescent spectra to be detected by the sensor 56. For example, optical system 61 can include a convex lens. The band-pass filter 63 can be arranged as selectable filters which allow different areas of a photoluminescence spectra to be analyzed. The optical system 61 and band-pass filter 63 can also supply focused and/or collimated beams of photoluminescent radiation to be measured by the sensor 56.

As noted, the measurement tool 100 includes an optical mirror 58 such as a dichoric mirror, which is used to redirect incident illumination from light source 50 to the optical system 57 and which also allows photoluminescent radiation received at the optical system 57 to pass through the optical mirror 58 to the sensor 56 through the optical system 61 and band-pass filter 63. The tool 100 can also include a non-reflective lid 18 which is used to protect users of a tool 100 from optical radiation. The radiating beam supplied by light source 50, which is collimated, can have a spot diameter of less than about 5 millimeters, for example, a spot diameter of about 1 millimeter. This would be particularly suitable for irradiating a cadmium telluride semiconductor material absorber layer 21. Light from the light source 50 could also be focused towards the cadmium sulfide semiconductor window material layer 19 in which case a spot diameter in the range of about 100 um to about 500 um can be used.

Figure 5:
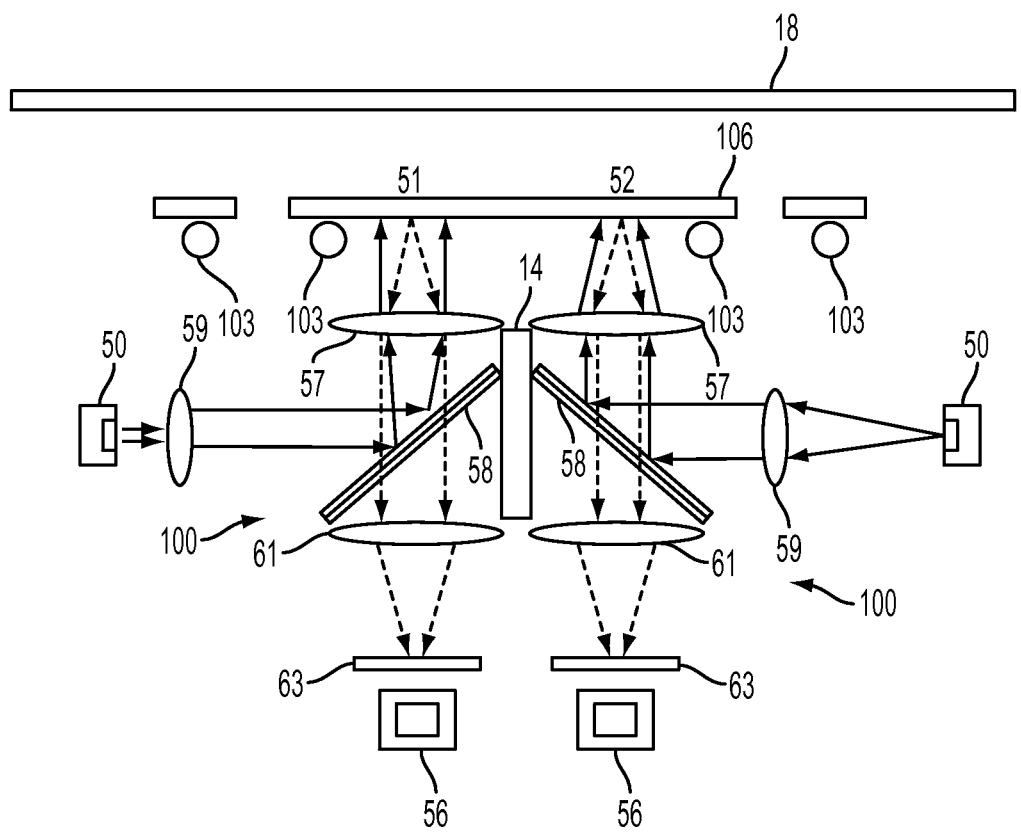
FIG. 5 illustrates another photoluminescence tool which can be used in an embodiment of the invention.

FIG. 5 illustrates an embodiment employing two tools 100 which can be used to obtain photoluminescence spectra for different ones of the semiconductor window layer 19 e.g., CdS, absorber layer 21 e.g., CdTe and interface e.g., $CdS_xTe_{1-x}$ between them by employing different excitation wavelengths and/or intensity at the respective light sources 50 and/or by choosing different focal positions for the optical system 57. In order to maintain separation between the two tools 100 a light barrier 14 can be provided. With the arrangement shown in FIG. 5, each of the respective tools 100 can be used to excite a different layer or combination of layers of semiconductor layer, e.g., CdS, CdTe or $CdS_xTe_{1-x}$, in the completed photovoltaic device 106 with a respective excitation wavelength and/or filtered photoluminescence spectra and with a corresponding different photoluminescent spectra being sensed by the respective sensors 56. The two tools 100 can also be used to excite the same semiconductor layer with different light wavelengths and with the same or different reception band-pass filter 63, if desired.

Figure 6:
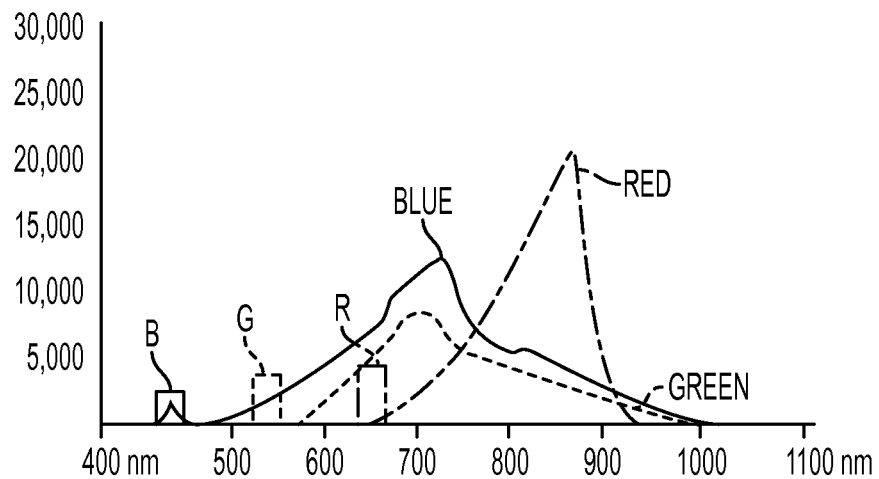
FIG. 6 illustrates a diagram showing excitation and resultant photoluminescence response spectra employed in various embodiments of the invention.

One manner in which the excitation light source 50 and resulting photoluminescence spectra intensity from a completed photovoltaic device 106 can be used to analyze processing conditions such as Cu doping concentration at stage 111, and the temperature of the metallization heat treatment at stage 115 is now explained in connection with FIGS. 6, 7 and 8. FIG. 6 shows light source 50 excitation and wavelength with blue (B), green (G) and red (R) excitation wavelengths and the resulting BLUE, GREEN and RED photoluminescent spectra. The wavelengths of both the excitation signal and the photolumination spectra are illustrated along the x-axis while the y-axis illustrates the photoluminescence intensity in terms of photoluminescence photon counts detected by sensor 56.

Figure 6A:
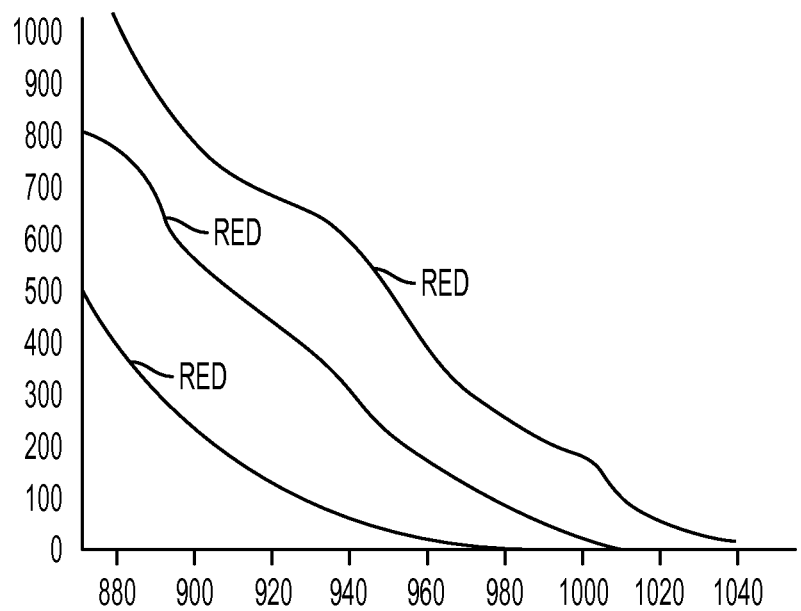
FIG. 6A shows an enlargement of the tail portion of the spectra shown in FIG. 6 for the color red excitation.

FIG. 6A illustrates an enlarged portion of the RED spectra tail from wavelengths 880 nm to 1040 nm and shows the different spectra which have been absorbed depending on variations to Cu doping concentration at stage 111 (FIG. 3) or temperature changes at stage 115 (FIG. 3). Similar changes occur in the BLUE spectra with changes in processing temperature at heat treatment stage 115 have also been observed. The correlation in the spectra with Cu doping concentration at stage 111 and temperature changes at stage 115 are now explained with reference to FIGS. 7-9.

Figure 7:
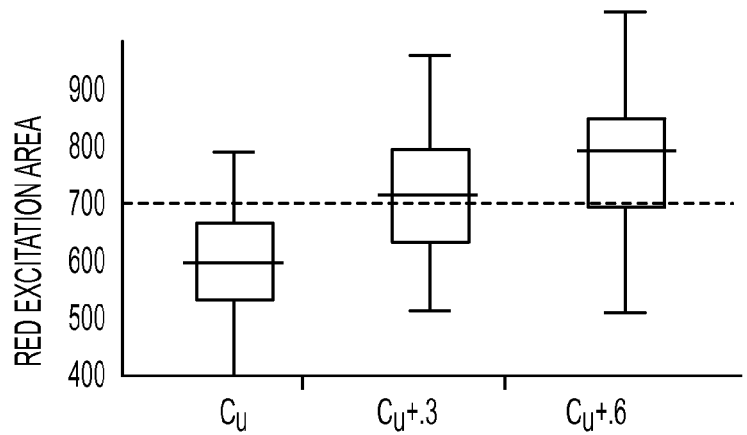
FIG. 7 illustrates the relationship between a red excitation photoluminescence response spectra and a copper doping concentration.

FIG. 7 illustrates with a box diagram a correlation between a tail portion of a red photoluminescent spectra and a copper doping concentration. The wavelength range for the tail spectra is about 900 nm to about 1100 nm. The box represents the majority of count values as a light intensity signature taken over a plurality of sample locations of the completed photovoltaic device 106. The upper and lower horizontal surfaces of each box represent the range of 25% to 75% of the collected data. The horizontal lines through each box represents the median of the collected data. The horizontal lines above and below the boxes indicate the highest and lowest observed count values. As shown, as the copper used in the doping stage 111 increases from Cu to Cu+0.3 (parts per million (ppm)) to Cu+0.6 (ppm), the photoluminescent count at the tail portion of red photoluminescence spectra likewise increases. As a result, the tool 100 illustrated in FIG. 4 can be used to determine the level of Cu doping concentration in doping stage 111 and any deviations of the Cu doping concentration from a desired reference doping concentration.

Figure 8:
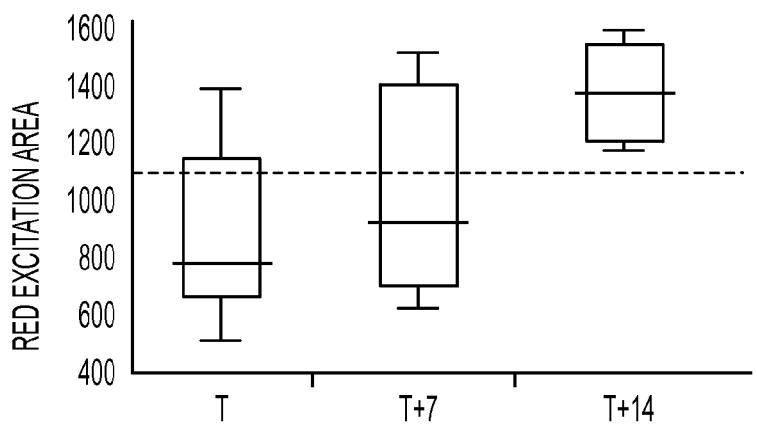
FIG. 8 illustrates the relationship between a red excitation photoluminescence response spectra and a processing temperature.

FIG. 8 shows how the tail portion of a red photoluminescence spectra PL in the wavelength range of about 900 nm to about 1100 nm can be used as an indicator of the temperature (in degrees centigrade) used in heat treatment stage 115. Here, an incurring light intensity signature in the form of an increasing count value represented by the sampled locations of a completed photovoltaic device 106 corresponds to an increase in temperature from a desired temperature T.

Figure 9:
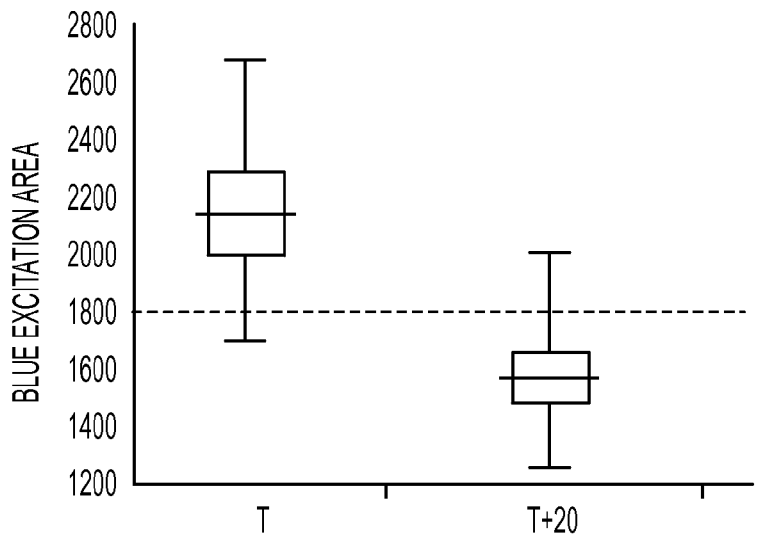
FIG. 9 illustrates the relationship between a blue excitation photoluminescence response spectra and a processing temperature.

Similarly, different spectra is observed in the (FIG. 6) BLUE spectra with temperature changes at heat treatment stage 115. FIG. 9 illustrates area under blue photoluminescence spectra in the range of about 650 nm to about 800 nm in terms of a box diagram which illustrates where the majority (25% to 75%) of detected photons accrue. As illustrated, the area of the blue photoluminescent spectra between about 650 to about 800 nm shows a light intensity signature having a decrease in count value corresponding to an increase in the temperature used in the heat treatment stage 115, with T representing a desired temperature. As can be seen, a higher photon count distribution is obtained when the temperature of the heat treatment stage 115 is operating at a desired temperature of T, as compared with the count value obtained when heat treatment stage 115 is operating at the temperature of T+20 degrees centigrade. This correlation between the area of the photoluminescent spectra of the blue excitation, and the temperature of the heat treatment stage 115 provides an indication of the temperature at which the heat treatment stage 115 is operating as well as any deviations from a desired temperature T.

Figure 10:
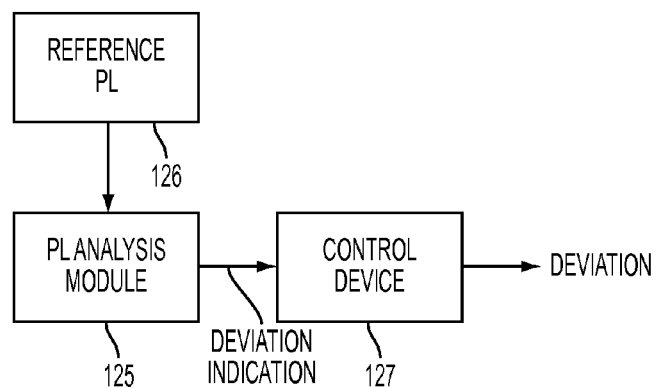
FIG. 10 illustrates use of a photoluminescent response spectra in an embodiment of the invention.

FIG. 10 illustrates a photoluminescence count analysis module 125 which receives a photon count value from a tool 100 over the wavelength set by tool 100 and from a plurality of sample locations on the completed photovoltaic device 106. The analysis tool accumulates the photon count values over the wavelength of interest to develop light intensity signature data such as illustrated in FIGS. 7, 8 and 9 and can determine median values. A reference count value PL which represents a count value from a plurality of like locations and which is expected for proper Cu doping at Cu doping stage 111, or for proper heat treatment temperature at heat treatment 115, is also received by module 125. A deviation in the detected and reference median photon count values is indicated by an output of analysis module 125. The output indication can be audibly or visually indicated to an operator for action, or could be used as a control signal to a control device 127 to adjust the operating parameter of Cu doping at stage 111 or temperature of heat treatment at stage 115.

Figure 11:
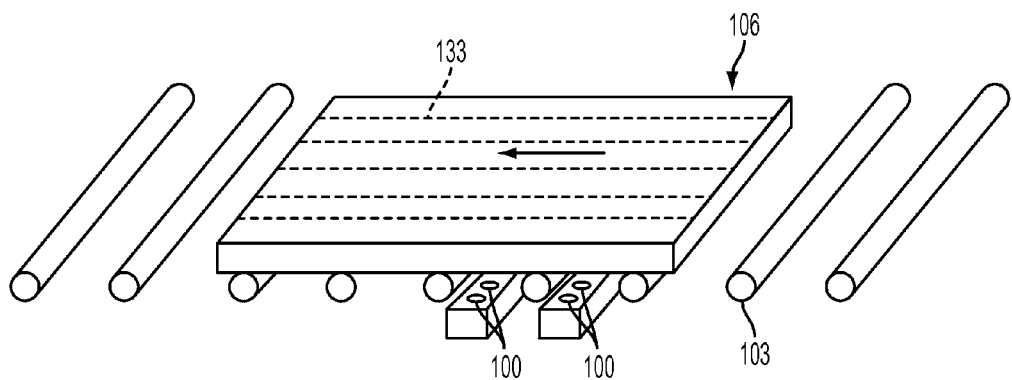
FIG. 11 illustrates a photovoltaic device undergoing a photoluminescent inspection.

FIG. 11 illustrates a variation of the FIG. 5 embodiment in which the plurality of tools 100 are spaced from one another in both the lengthwise and widthwise direction of a completed photovoltaic panel 106 to gather information from a plurality of widthwise and lengthwise sample locations 133 as the completed photovoltaic device 106 passes over the tools 100. The plurality of sampling points 133 are used to gather photon counts of the photoluminescent spectra cover a set wavelength range. The photon count values from the various tools 100 can be summed to provide the output spectra illustrated in FIG. 6 for different wavelengths of excitation signals and for a plurality of locations of a passing completed device 106.

Figure 12:
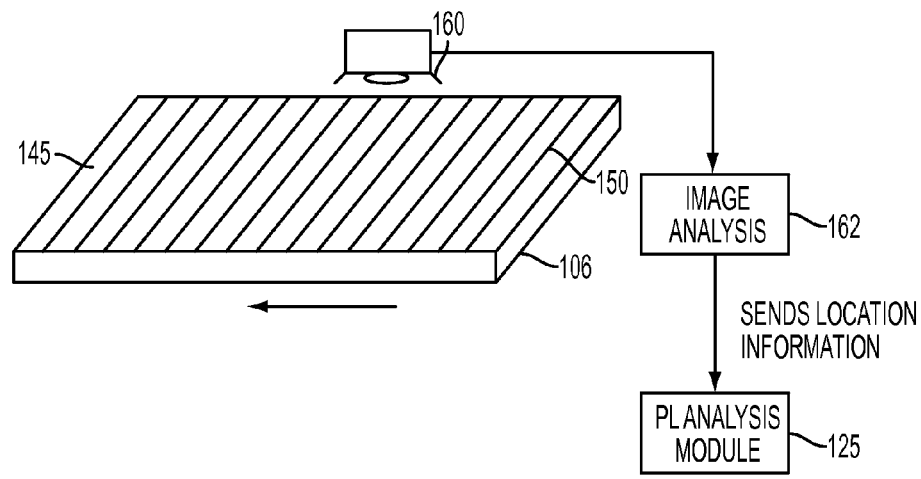
FIG. 12 illustrates an image analysis system which can be used in another embodiment of the invention.

As shown in FIG. 12, in many instances, the completed photovoltaic device 106 will have a plurality of photovoltaic cells 145 therein which are separated by scribe lines 150 which pass through one or more semiconductor material layers and which may therefore interfere with the collection of photons. Accordingly, counting photons at such locations should be avoided. FIG. 12 illustrates an embodiment in which the scribe lines are eliminated from the sampling locations 133 illustrated in FIG. 11. The scribe lines are visible through a glass back panel 25 (FIG. 2). In FIG. 12 an imaging camera 160 is used to take an image of a completed photovoltaic device 106 showing the location of the scribe lines 150. The image is fed to an image analysis device 162 which identifies the locations of the scribe lines 150 on the passing device 106. This information is then passed to the analysis module 125 so that any photon collection taken at locations corresponding to the scribe lines are removed from the collected count results before they are used for analysis, for example, compared to the reference photoluminescence spectra (FIG. 10). Alternatively, the light source 50 of one or more tools 100 can be controlled so that it is not irradiating the completed photovoltaic device 106 when a scribe line 150 passes by the focal point of the irradiating light as the completed photovoltaic device 106 moves past a tool 100. As another alternative, the location of the scribe lines can be fed to a tool 100 to control the gating of photons to sensor 56 such that no photons are collected from the location of the scribe lines 150.

Figure 13:
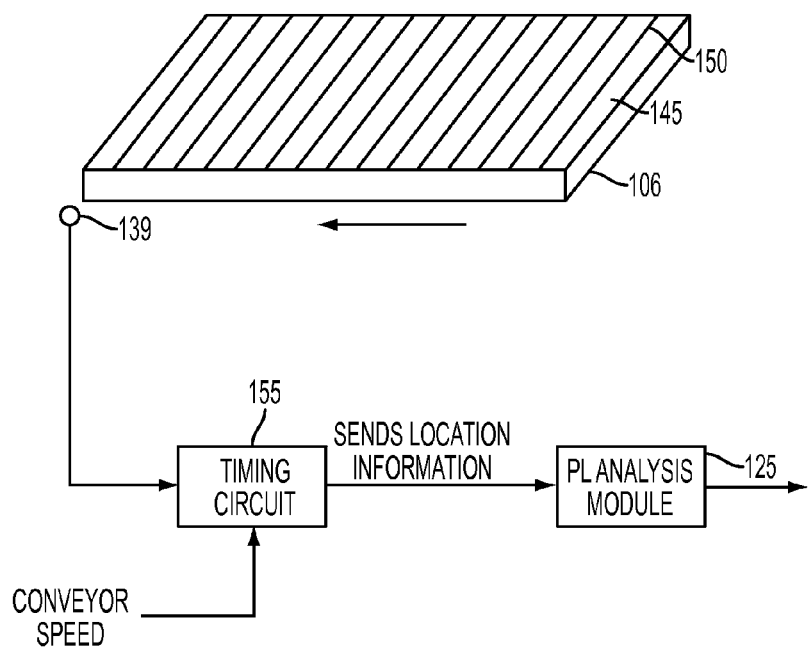
FIG. 13 illustrates a photovoltaic device edge detection system which can be used in another embodiment of the invention.

FIG. 13 illustrates another example of an embodiment which can eliminate photon collection at the location of the scribe lines 150. In this embodiment, an edge detector 139 is used to detect the leading edge of the completed photovoltaic device 106. Information on the detected leading edge is fed to a timing circuit 155 along with information on conveyer speed which provides an output signal to the analysis module 125 indicating specific locations of the scribe lines 150 as they pass over a tool 100 which can again be fed to analysis module 125 or a gating control on a tool 100 such that any photon data from the scribe locations is eliminated from the accumulating count value, or the light source 50 does not emit light when a scribe line passes by a tool 100.

Various embodiments of the invention have been described which can use photoluminescence spectra information obtained from a completed photovoltaic device 106 to determine whether a process operating parameter is within prescribed operating conditions or deviates therefrom. The specific operating parameters of copper doping concentration and temperature variations in the stages 111 and 115 illustrated in FIG. 3 have been described. However, the invention can also be used to measure a photoluminescence signal from a completed photovoltaic device 106 for other operating parameters to determine whether such other operating parameters are within desired values or deviate from desired values. Also, although embodiments have been disclosed where tool 100 is located after a bias stage 119 (FIG. 3), tool 100 can also be located at any point following the processing of the internal material layers of a completed photovoltaic device 106, including before the back cover 25 is applied or after final assembly stage 117, but before the bias stage 119. Accordingly, the invention is not limited by the foregoing description and is only limited by the scope of the appended claims.

What is claimed as new and desired to be protected by Letters Patent of the United States is:

1. A method of determining a processing characteristic of photovoltaic device fabrication, the method comprising:
   receiving a substrate which has a chloride treated absorber layer thereon;
   further processing the substrate having the chloride treated absorber layer;
   illuminating the processed substrate with light of a predetermined wavelength;
   determining the intensity of photoluminescent light produced by the processed substrate; and
   forming a photoluminescent light intensity signature based on the intensity of the photoluminescent light,
   wherein further processing the substrate comprises forming a back contact on the absorber layer, heat treating the back contact, and utilizing the intensity of the photoluminescent light to detect deviations in temperature during the heat treating of the back contact.

2. A method as in claim 1, wherein the intensity of photoluminescent light is detected at a plurality of locations on the substrate.

3. A method as in claim 2, further comprising:
   comparing a photoluminescent light intensity signature for the substrate with a reference photoluminescent light intensity signature to characterize a processing condition of the further processed substrate.

4. A method as in claim 1, wherein the light source produces red light.

5. A method as in claim 1 wherein the light source produces blue light.

6. A method as in claim 1, wherein the light source produces green light.

7. A method as in claim 1, further comprising moving the processed substrate relative to at least one photodetector which receives photoluminescent light from the processed substrate.

8. A method as in claim 7, wherein the photodetector is stationary and the photovoltaic substrate is moved past the photodetector.

9. A method as in claim 1, wherein further processing the substrate comprises doping the absorber layer and utilizing the intensity of the photoluminescent light to detect a doping concentration of the absorber layer.

10. A method as in claim 9, wherein the doping comprises copper doping.

11. A method as in claim 2, further comprising forming the light intensity signature by combining the detected photoluminescent light intensity from the plurality of locations.

12. A method as in claim 2, wherein the plurality of locations are provided along the length and width of the substrate.

13. A method as in claim 1, wherein the processed substrate is part of a completed photovoltaic device, the completed photovoltaic device being illuminated through the substrate by the light of the predetermined wavelength.

14. A method as in claim 13, wherein the completed photovoltaic device includes scribe lines which define photovoltaic cells, the method further comprising identifying the location of the scribe lines and forming the photoluminescent light intensity signature based on a plurality of locations on the completed photovoltaic device, not including at the locations of the scribe lines.

15. A method as in claim 1, wherein the predetermined wavelength is determined by at least one of the type of light source and a band-pass filter.

16. A method as in claim 1, further comprising band-pass filtering the photoluminescent light before determining the intensity.

17. A method as in claim 1, wherein the substrate comprises a CdS window layer and a CdTe absorber layer.

18. A method as in claim 1, further comprising lines bias conditioning the substrate after completion of the further processing and wherein the substrate is illuminated after the bias conditioning.

19. A method as in claim 1, further comprising lines bias conditioning the substrate after completion of the further processing and wherein the substrate is illuminated before the bias conditioning.

20. A method as in claim 1, wherein the illumination and detecting are done in line in a photovoltaic device manufacturing line.

21. A method of inspecting a completed photovoltaic device comprising a heat treated back contact, the method comprising:
    illuminating the photovoltaic device through a light receiving surface with light of a predetermined wavelength;
    determining the intensity of photoluminescent light produced by the photovoltaic device;
    forming a photoluminescent light intensity signature for the photovoltaic device,
    utilizing the intensity of the photoluminescent light to detect deviations in temperature during heat treating of the back contact.

22. A method as in claim 21, wherein the predetermined wavelength is a wavelength of red light.

23. A method as in claim 21, wherein the predetermined wavelength is a wavelength of blue light.

24. A method as in claim 21, wherein the predetermined wavelength is a wavelength of green light.

25. A method as in claim 21, further comprising moving the completed photovoltaic device past a fixed tool containing a source of illumination and a photoluminescent detector.

26. A method as in claim 21, further comprising using the light intensity signature to determine a parameter used in a process of fabricating the completed photovoltaic device.

27. A method as in claim 26, wherein the parameter is a doping concentration of an absorber layer within the completed photovoltaic device.

28. A method as in claim 27, wherein the doping concentration is a copper doping concentration.

29. A method as in claim 22, wherein the intensity of the photoluminescent light is determined in the wavelength range of about 900 nm to about 1100 nm.

30. A method as in claim 23, wherein the intensity of the photoluminescent light is determined in the wavelength range of about 650 nm to about 800 nm.

* * * * *